United States Patent [19]
Larsson

[11] Patent Number: 5,081,661
[45] Date of Patent: Jan. 14, 1992

[54] X-RAY EXAMINATION APPARATUS

[75] Inventor: Sten Larsson, Vaellingby, Sweden

[73] Assignee: Siemens Aktiengesellschaft, Munich, Fed. Rep. of Germany

[21] Appl. No.: 585,521

[22] Filed: Sep. 20, 1990

[30] Foreign Application Priority Data

Sep. 27, 1989 [SE] Sweden .............................. 89031751

[51] Int. Cl.⁵ .............................................. H05G 1/02
[52] U.S. Cl. .................................. 378/197; 378/196; 378/193
[58] Field of Search ............... 378/196, 197, 195, 198, 378/193, 11, 15, 17, 38–40, 204–209, 194

[56] References Cited

U.S. PATENT DOCUMENTS

| | | | |
|---|---|---|---|
| 3,838,287 | 9/1974 | Barrett et al. | 378/196 |
| 4,635,284 | 1/1987 | Christiansen | 378/197 |
| 4,716,581 | 12/1987 | Barud | 378/198 |
| 4,918,716 | 4/1990 | Hahn | 378/197 |
| 4,922,512 | 5/1990 | Lajus et al. | 378/197 |
| 4,979,202 | 12/1990 | Siczek et al. | 378/197 |

FOREIGN PATENT DOCUMENTS 260846 1/1976 Fed. Rep. of Germany .

Primary Examiner—Janice A. Howell
Assistant Examiner—Kim-Kwok Chu
Attorney, Agent, or Firm—Hill, Van Santen, Steadman & Simpson

[57] ABSTRACT

An x-ray examination apparatus has a bent carrier having a first end to which a radiation source is attached and a second end to which an x-ray image intensifier is connected. The radiation source and the image intensifier are respectively connected to the carrier via individual, laterally projecting booms. Each boom is connected to the carrier so as to be rotatable around an axis at the end of the carrier to which it is connected. The arrangement allows unimpacted accessibility to the patient in different types of examinations.

6 Claims, 2 Drawing Sheets

X-RAY EXAMINATION APPARATUS

BACKGROUND OF THE INVENTION

1. Field of the Invention

The present invention is directed to an x-ray examination apparatus of the type having a bent carrier having one end at which at which radiation source is mounted and an opposite end to which an image intensifier is mounted.

2. Description of the Prior Art

An x-ray examination apparatus is disclosed in German OS 26 08 461 of the type wherein and x-ray source and an x-ray image intensifier are respectively mounted at opposite ends of a bent carrier, with the carrier being supported by a height-adjustable holder.

It is important in conducting x-ray examinations, for example in combination with a catheterization, that the physician have good accessibility to the patient. In such examinations, the examination table and the x-ray examination stand are usually displaceable parallel to each another, so that the radiation source and the x-ray image intensifier are displaceable between the foot end and the head end of the examination table. Such accessibility to the patient is not always present, because the stand, including the carrier which may be C-shaped, V-shaped or U-shaped, may be an impediment in certain examinations. This can be the case, for example, if a catheter is introduced into a guide and is pushed downwardly into a leg. For this procedure, the physician must stand at the same side of the patient support at which the pedestal for the carrier is attached. If the radiation source and the image intensifier follow the path of the catheter, or of the contrast agent, for imaging, the stand will move toward the physician.

SUMMARY OF THE INVENTION

It is an object of the present invention to provide an x-ray examination apparatus of the type having a bent carrier with a radiation source at one end and an x-ray image intensifier at an opposite end, which permits good accessibility to the patient in various types of examinations. The above object is achieved in accordance with the principles of the present invention in an x-ray examination installation wherein the x-ray source is mounted to one end of the carrier by a boom which is rotatable around an axis at the carrier end, and the x-ray image intensifier is also mounted on a boom which is rotatable around an axis at the opposite end of the carrier. The physician can thus decide at which side of the boom for the radiation source or the boom for the image carrier he or she wishes to be situated. A further advantage is that, if the apparatus is of the type which is movable along the floor or ceiling parallel with the examination table the apparatus must be conveyed over a shorter path than conventional installations, and as a result occupies less space in the examination room, because the radiation source and the x-ray image intensifier have a greater range of movement.

In a further embodiment of the invention, the x-ray image intensifier and the radiation source are each rotatable around respective second axes, so that these components can be directed toward each other at all positions of the booms. Such a second axis is preferably employed if the carrier is V-shaped, and if the axes of the booms are not arranged in axial alignment, or parallel to one another.

In a further embodiment, the x-ray image intensifier or the radiation source may be rotatable by a drive mechanism. The drive mechanism may maintain one of the components in automatic alignment with the other.

In a further embodiment of the invention, the booms may be synchronously rotatable by drive mechanisms, so that the radiation source and the image intensifier can be quickly brought to a desired position.

DESCRIPTION OF THE PREFERRED EMBODIMENTS

Figure 1:
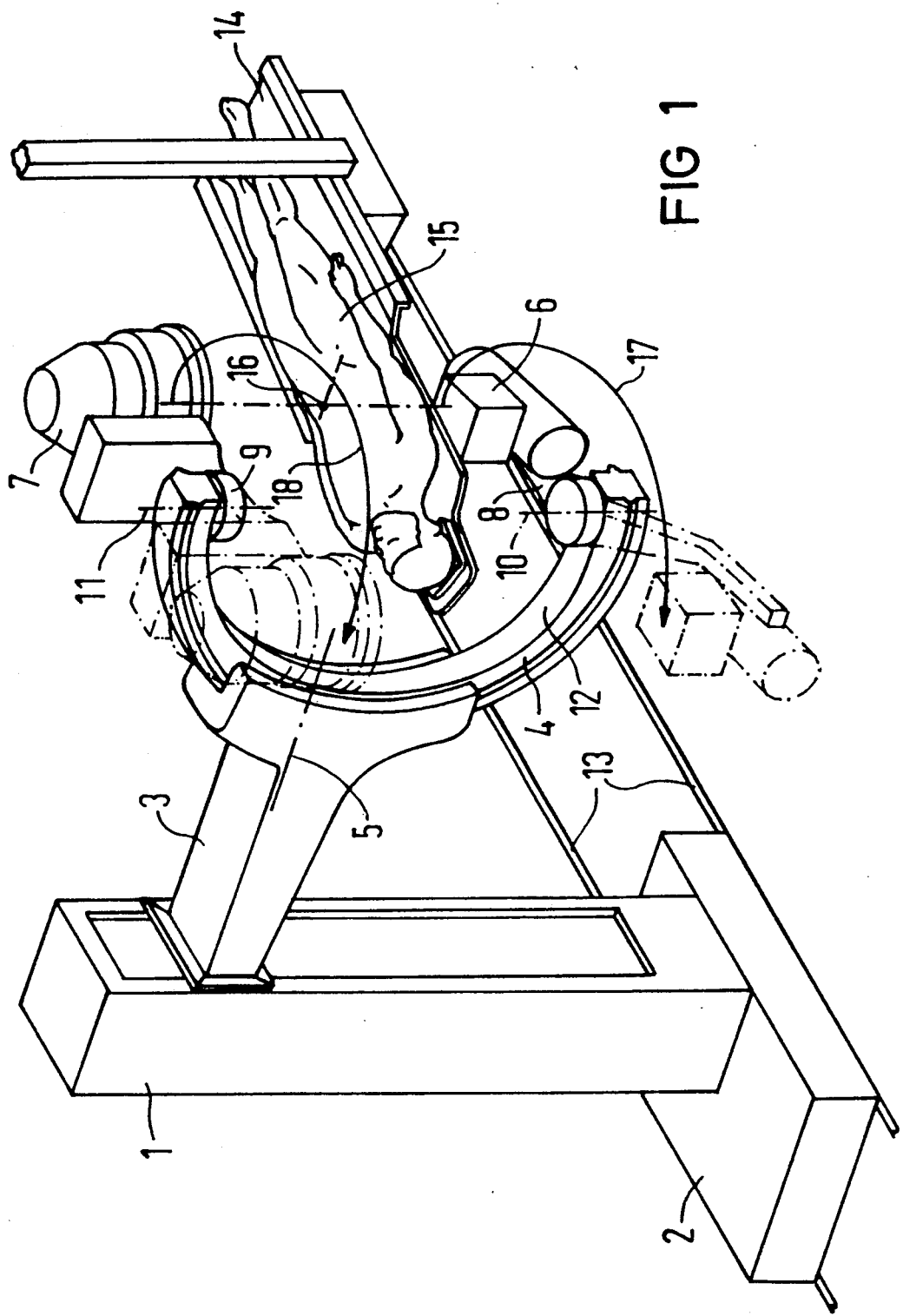
FIG. 1 is a perspective view of an x-ray examination apparatus constructed in accordance with the principles of the present invention.

An x-ray examination apparatus in a first embodiment constructed in accordance with the principles of the present invention is shown in FIG. 1 The apparatus includes a support column 1 attached to a support carriage 2. A holder 3 for a bent carrier 4 is situated at the support column 1 and is attached so as to be longitudinally displaceable relative thereto. (As used herein, the term "bent" carrier means a carrier which is, for example, C-shaped, V-shaped or U-shaped.)

The holder 3, and thus the carrier 4 as well, are seated so as to be pivotable around a horizontal axis 5. An x-ray tube 6 is mounted at one end of the carrier and an x-ray image intensifier 7 is mounted at the other end aligned with the x-ray tube. The x-ray tube 6 is attached to the carrier 4 via a projecting boom 8, and the x-ray image intensifier 7 is connected to the carrier via a projecting boom 9. The booms 8 and 9 are also connected to the inside surface 12 of the carrier 4 so as to be rotatable around respective vertical axes 10 and 11, which are in axial alignment with each other. The carrier 4 is also mounted so as to be displaceable along the bend. The holder 3 leaves the inside surface 12 of the carrier 4 unimpeded over its entire length. The support carriage 2 is movable on floor rails 13.

The support carriage 2, the holder 3 and the carrier 4 can execute prescribed motion sequences by means of a control system of the type described, for example, in the aforementioned German OS 34 13 348. These motion sequences cause the x-ray tube 6 and the x-ray image intensifier 7 to move in a spherical pattern around an imaginary isocenter, for example, around the point 16 of a patient 15 resting on an examination table 14. The support carriage 2 in combination with the support column 1 can be moved parallel to, and along, the examination table 14.

The x-ray tube 6 and the x-ray image intensifier 7 can be rotated via the respective booms 8 and 9 around the axes 10 and 11 through, for example, 180°, as indicated by the arrows 17 and 18. The x-ray tube 6 and the x-ray image intensifier 7 can thus be moved off-center, relative to the carrier 4, in a mirror-symmetric manner. This further position of the x-ray tube 6 and the x-ray image intensifier 7 is shown in FIG. 1 in dot-dash lines.

In this position, it is also possible to move the x-ray tube 6 and the x-ray image intensifier 7 in a spherical motion pattern around an imaginary isocenter using the control system. The movement may ensue synchronously by means of interrelated drive mechanisms (not shown). The physician can therefore decide at which location he or she must stand to conduct a particular type of examination, and can position the x-ray tube 6 and/or the x-ray image intensifier 7, based on the various movement possibilities, at a location which does not impede the examination.

In a known manner, movement of the x-ray tube 6 and the x-ray image intensifier 7 can be stopped at any arbitrary position, so that the examination can be undertaken as needed.

The axes 10 and 11 of the booms 8 and 9 may alternatively be disposed parallel to each other. In such an embodiment, however, the x-ray tube 6 and the x-ray image intensifier and/or the booms 8 and 9 should be controlled by related drive mechanisms so that the x-ray tube 6 and the x-ray image intensifier 7 are aligned to each other at each position.

Figure 2:
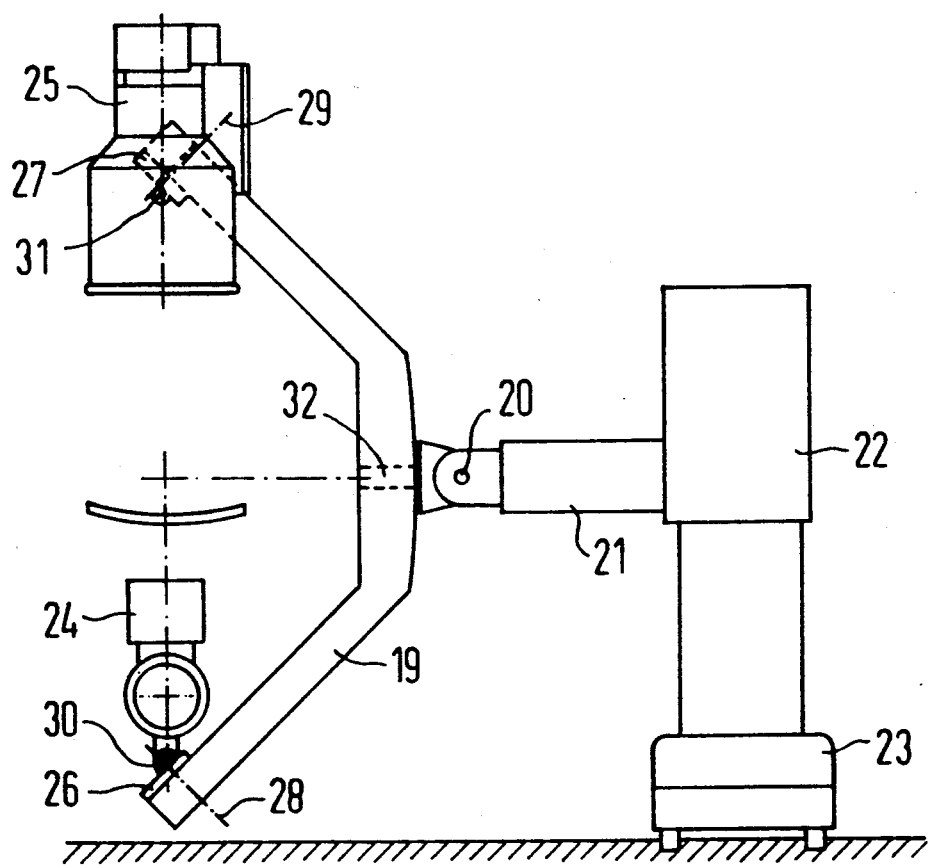
FIG. 2 is a side elevational view of a further embodiment of an x-ray examination apparatus constructed in accordance with the principles of the present invention.

A further embodiment of the apparatus is shown in FIG. 2 having a U-shaped or V-shaped carrier 19, having an x-ray tube 24 and an x-ray image intensifier 25 mounted thereto, and which is connected to a holder 21 via a connecting point. The holder 21 is in turn mounted in height-adjustable fashion to a support column 22, which is attached to a support carriage 23. The carrier 19 can be swiveled around a horizontal shaft 32. Such an apparatus is described in greater detail in German OS 34 13 348. In this embodiment, the x-ray tube 24 is mounted to the carrier 19 via a projecting boom 26, and the x-ray image intensifier 25 is mounted to the carrier via a projecting boom 27. The booms 26 and 27. The booms 26 and 27 are mounted to the carrier 19 so as to be swivelable around respective axes 28 and 29. Because the axes 28 and 29 do not lie in axial alignment with each other, and are not parallel to each other, the x-ray tube 24 and the x-ray image intensifier 25 are respectively rotatable around second axes 30 and 31 so that the x-ray tube 24 and the x-ray image intensifier 25 can be aligned to each other at each position of the booms 26 and 27. Rotation around the axis 30 and 31 can be undertaken by a drive mechanism supplemented by the control system disclosed in German OS 34 13 348.

Although modifications and changes may be suggested by those skilled in the art, it is the intention of the inventor to embody within the patent warranted hereon all changes and modifications as reasonably and properly come within the scope of his contribution to the art.

I claim as my invention:

1. An x-ray examination apparatus comprising:
   a bent carrier having first and second ends, and means for supporting said carrier in an examination room;
   a first boom mounted to laterally project from said carrier at said first end of said carrier, said first boom being rotatable around a first axis at said first end of said carrier;
   an x-ray source mounted to said first boom;
   a second boom mounted at said second end of said carrier to laterally project from said carrier, said second boom being mounted so as to be rotatable around a second axis at said second end of said carrier; and
   an x-ray image intensifier mounted on said second boom.

2. An x-ray examination apparatus as claimed in claim 1 wherein said first and second axes are in axial alignment with each other.

3. An x-ray examination apparatus as claimed in claim 1 wherein said first and second axes are disposed parallel to each other, and wherein movement of said x-ray source and said x-ray image intensifier are controlled by drive mechanisms.

4. An x-ray examination apparatus as claimed in claim 1 wherein said x-ray source is mounted on said first boom so as to be rotatable around a third axis and wherein said x-ray image intensifier is mounted on said second boom so as to be rotatable around a fourth axis so that said x-ray source and said x-ray image intensifier can be aligned to each other at all positions of said booms.

5. An x-ray examination apparatus as claimed in claim 4 wherein said x-ray image intensifier and said x-ray source are each rotatable respectively around said third and fourth axes by respective drive mechanisms.

6. An x-ray examination apparatus as claimed in claim 1 wherein said booms are synchronously rotatable by drive mechanisms.

* * * * *